United States Patent [19]

Chou et al.

[11] Patent Number: 4,995,068
[45] Date of Patent: Feb. 19, 1991

[54] RADIATION THERAPY IMAGING APPARATUS

[75] Inventors: T. Jason Chou, Fayetteville; Harold Shoenfeld, Brooklyn; William C. Greenway, Liverpool, all of N.Y.

[73] Assignee: S&S Inficon, Inc., Liverpool, N.Y.

[21] Appl. No.: 415,994

[22] Filed: Oct. 2, 1989

[51] Int. Cl.⁵ .................. H01J 31/49; A61B 6/00; G01N 23/04
[52] U.S. Cl. .................. 378/189; 378/19; 378/190; 378/62
[58] Field of Search .................. 378/62, 63, 64, 65, 378/68, 69, 4, 19, 20, 205, 206, 209, 99, 189, 205, 190, 4, 19

[56] References Cited

U.S. PATENT DOCUMENTS

| | | | |
|---|---|---|---|
| 4,355,331 | 10/1982 | Georges et al. | 378/99 |
| 4,890,313 | 12/1989 | Lam et al. | 378/65 |

FOREIGN PATENT DOCUMENTS

| | | | |
|---|---|---|---|
| 3447050 | 7/1986 | Fed. Rep. of Germany | 378/63 |
| 0158984 | 12/1979 | Japan | 378/63 |
| 0010600 | 1/1985 | Japan | 378/63 |

OTHER PUBLICATIONS

Munro et al., A Digital Fluoroscopic Imaging Device for Radiotherapy Localization, Am. Soc. for Therapeutic Radiology and Oncology, Oct. 9, 1988.
Munro et al., Therapy Imaging: A Signal-to-Noise Analysis of Metal Plate Film Detectors, 14 Med. Phys. 975, Nov. 1987.

*Primary Examiner*—Janice A. Howell
*Assistant Examiner*—Don Wong
*Attorney, Agent, or Firm*—Wall and Roehrig

[57] ABSTRACT

A radiation therapy imager provides images of a patient while being treated while on a radiation therapy machine for purposes of verification and monitoring of position and alignment, and for shaping of the radiation field. The radiation therapy imager has a video camera mounted on the gantry of the radiation therapy machine and positioned diametrically opposite the treatment head. An elongated light box is disposed over the camera to exclude ambient light from the camera and a fluoroscopic plate is positioned at the distal end of the light box, i.e., the end remote of the camera. The plate is aligned with and facing the head to produce a fluoroscopic image in response to the treatment radiation that is applied from the head through the patient. A mirror in the light box is oriented to reflect the image to the camera to permit monitoring on a viewing screen. The light box can be retracted from under the treatment table either by telescoping the light box down or by swinging the light box to one side. A remote console has the capability of inputting a simulator image of the patient from a simulator radiograph and displaying the simulator image and the therapy fluoroscopic image in a side-by-side or superimposed comparison. The images produced by the radiation treatment imager can be digitized, enhanced, displayed, and stored.

9 Claims, 5 Drawing Sheets

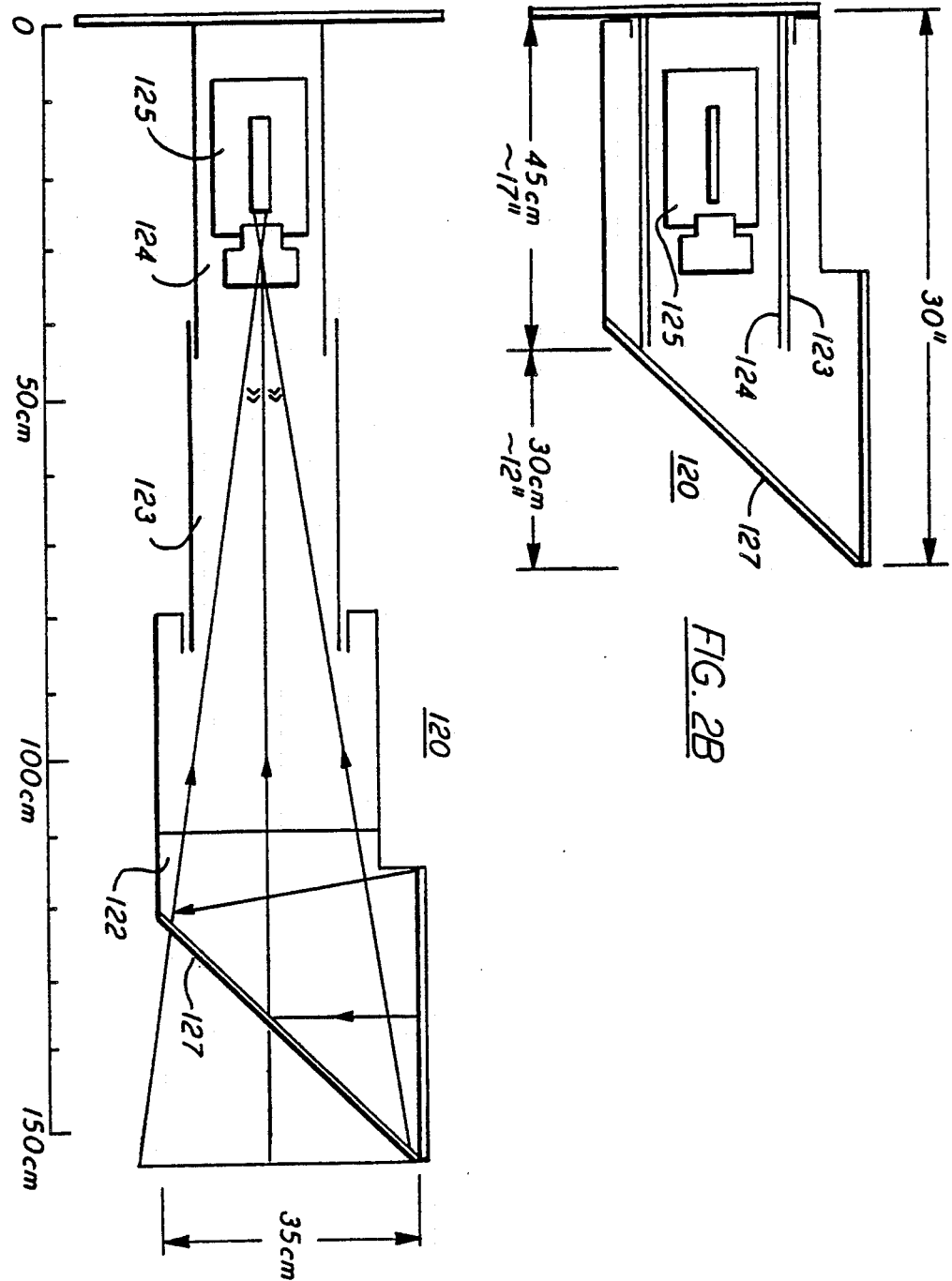

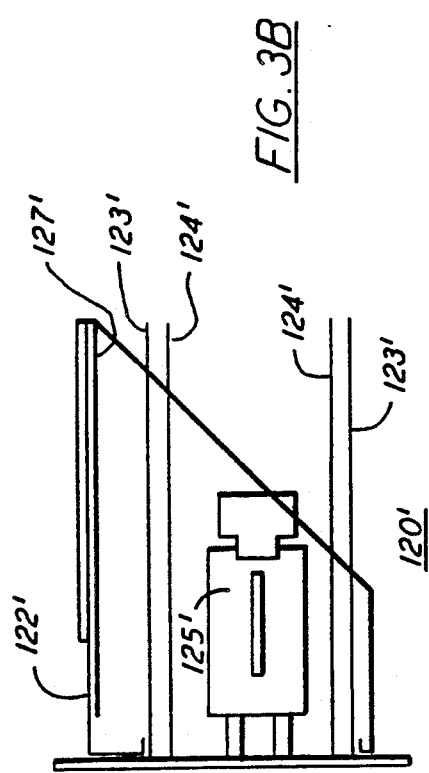
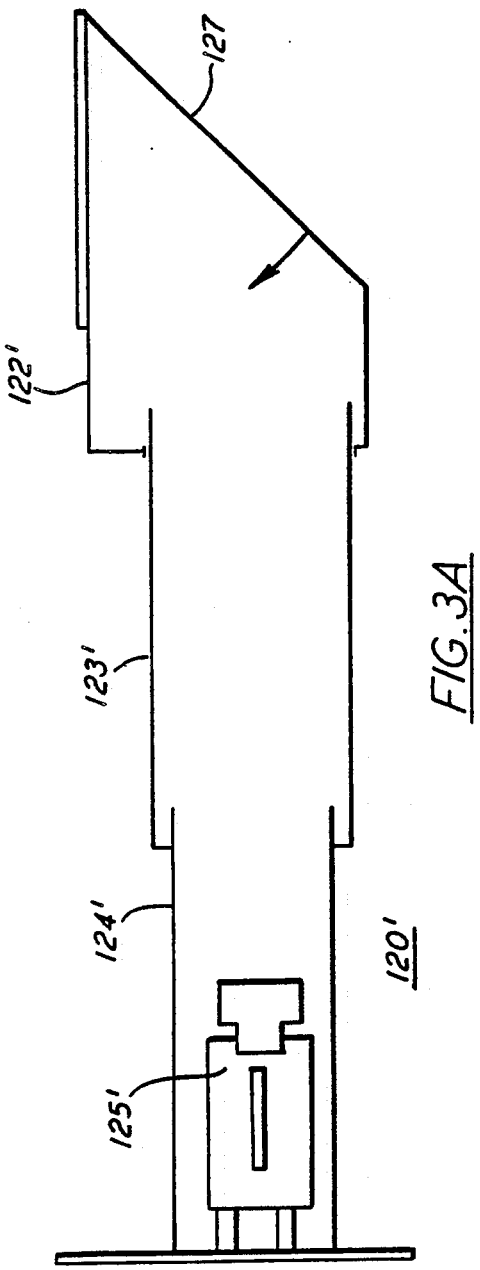

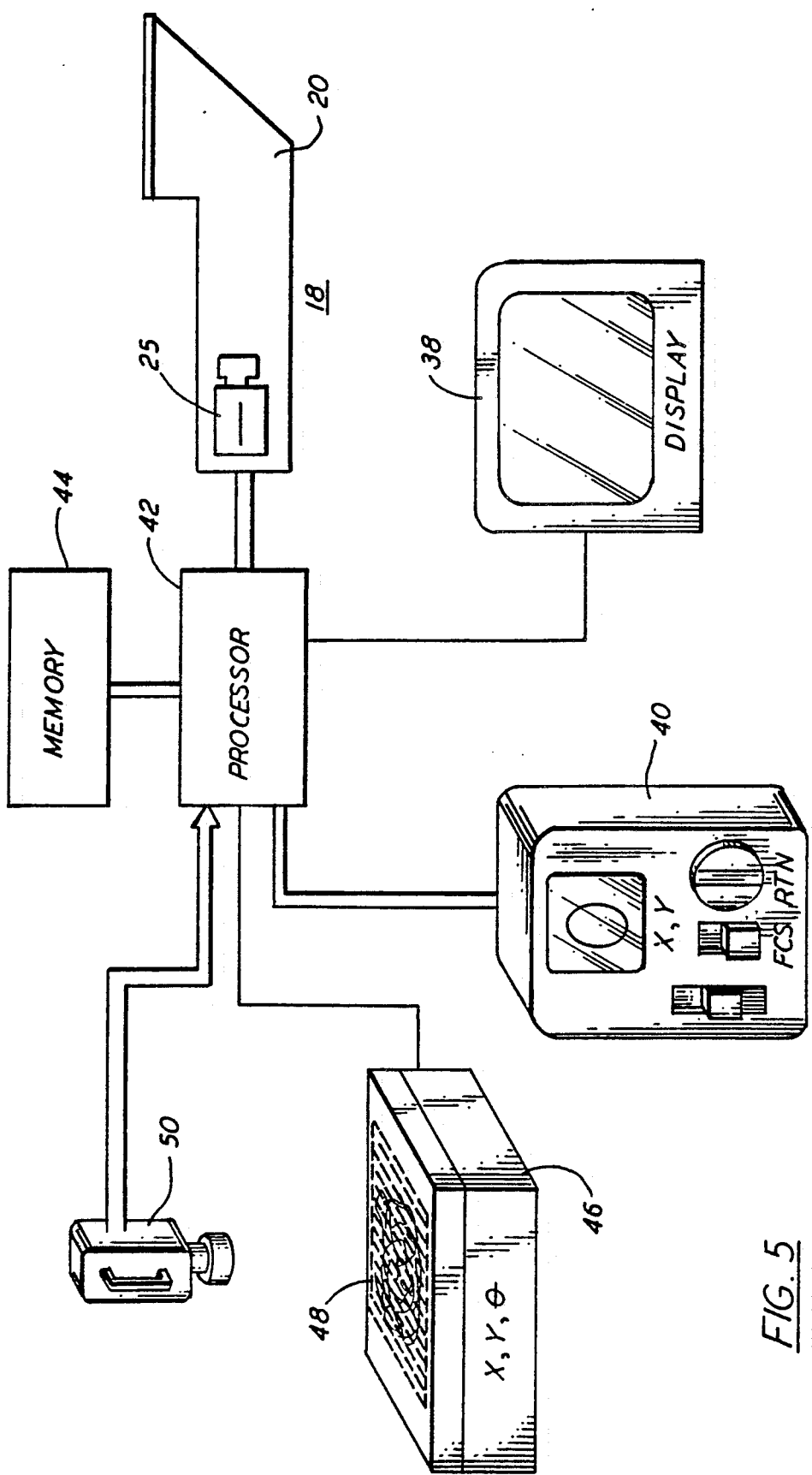

RADIATION THERAPY IMAGING APPARATUS

BACKGROUND OF THE INVENTION

This application relates to radiology and radiotherapy, and is more particularly directed to imaging devices for aligning and monitoring a treatment radiation field relative to a patient positioned on a treatment table.

Radiation therapy involves applying one or more doses per treatment of high-energy x-ray radiation to a patient. The strength of the radiation must be concentrated in a specific area, e.g. to control a tumor, but the total radiation to which the patient is subjected should be kept low as possible. It is the current practice, prior to radiation therapy, for the patient to be positioned on a simulator, that is, on a low-energy x-ray machine which is otherwise identical to the x-ray treatment machine. An x-ray image is exposed onto film at the simulator, and this simulator image shows a portion of the patients body which is to receive radiation treatment. Then, using the information obtained on the simulator, the oncologist can prescribe the appropriate dosage, and can outline how the treatment field is to be collimated. However, the collimation of the field is always an approximate measure, because the patient can never be positioned exactly the same on the therapy machine as on the simulator. Also, there is always some movement of the patient's internal tissues between simulator and treatment, and, for that matter, during treatment. This means that the prescribed dose must be applied to a greater area than the tumor, and this subjects much of the surrounding tissues to radiation.

Prior attempts to use the radiation from a treatment machine to produce images have resulted in low resolution and poor contrast response. Prior to this invention, a cassette film device had to used for therapy imaging which was inconvenient, requried labor and time to develop the film, and yielded poor image quality.

Because the images are of low quality, the inconvenience to use and the time required to monitor the position of the applied dosage field to develop the film the cassette film device is not widely used to align the therapy beam relative to the patient.

During set up of the treatment machine, there are normally several people, namely the patient, oncologist, and at least one technologist in the room around the treatment table. A video fluoroscopic device mounted on the gantry below the table would be in the way of the practitioners. However, if the device were not affixed onto the gantry, it would be difficult or impossible to align the device precisely with the treatment beam.

OBJECTS AND SUMMARY OF THE INVENTION

It is an object of this invention to provide immediate, and high-quality imaging for radiotherapy.

It is another object of this invention to provide verification of patient positioning during treatment, relative to the applied radiation dosage.

It is a further object of this invention to provide visual confirmation of the alignment and shaping of the therapy radiation field.

It is still another object of this invention to provide a real-time therapy imaging device which is compact, lightweight, and of simple design.

It is yet another object of this invention to provide a therapy imaging detector which can be withdrawn or retracted from the patient treatment table when the detector is not required for imaging.

It is yet another object of this invention to provide a easy means to compare the treatment image against the planned simulator images.

In accordance with one aspect of this invention, a radiation therapy imaging apparatus produces images of a patient that is being treated on a radiation therapy machine, and provides verification and monitoring of the patient positioning, verification of alignment, and shaping of the radiation field.

The radiation therapy machine with which the imaging apparatus is employed has a high-energy treatment head for applying a radiation dose to the patient that is positioned on a treatment table, and has a gantry that is rotatable about a isocentric axis. The gantry carries the treatment head and permits the radiation dose to be applied to the patient from any of a range of angles about the isocentric axis of the machine.

The radiation therapy imaging apparatus has a video camera that is mounted on the gantry diametrically opposite the treatment head, and an elongated light-excluding box or enclosure that is disposed over the camera to exclude ambient light from the camera. There is a fluoroscopic plate positioned at a distal end of the light box away from the camera, facing the treatment head and aligned with it. The fluoroscopic plate produces a fluoroscopic image in response to the radiation that is applied from the head through the patient. A mirror in the light box beneath the fluoroscopic plate, is oriented e.g., at a 45 degree angle, to reflect the image to the camera. This permits monitoring on a remote viewing screen of the position of the radiation field in respect to the patient. The light box can be constructed with a telescoping arrangement or with a hinged arrangement to permit retracting of at least a distal end of a light box from its in-use position opposite the treatment head. This retraction can take place without moving the camera, so that the camera always remains properly aligned. In this way the light box is kept from projecting under the treatment table when the patient is being positioned on the treatment table, and radiation imaging is not taking place.

A remote console that is associated with the radiation therapy imager displays the fluoroscopic image as picked up by the video camera. The console also includes a camera, an x-y translatable light table, and other appropriate equipment to input a simulator image of the patient, and to display the simulator image and the fluoroscopic image in juxtaposition, i.e., either superimposed or side-by-side for an on-line comparison of therapy image against the simulator image. The remote console preferably also includes sufficient memory to store a sequence of a fluoroscopic images in digital form.

The image detector can be quickly and smoothly extended into its imaging position and will remain accurately positioned in use. The apparatus does not introduce any delay in the patient set up time.

The image detector can be positioned on vertical rails on the gantry, so that the entire imaging apparatus can be moved radially, i.e., towards or away from the treatment head. This permits the height of the imaging plate to be adjusted and positioned as close as possible to the patient. Focus of the image is maintained without requiring any readjustment after installation. The design of this system is as simple as possible, keeping both production costs low and also meeting safety and other regulatory requirements. The fluoroscopic images can be digitally acquired at the remote console, which permits image processing for contrast enhancement and noise reduction.

The above and many other objects, features, and advantages, of this invention will be more fully understood from the ensuing description of a few selected preferred embodiments, which description should be read in connection with the accompanying Drawing.

BRIEF DESCRIPTION OF THE DRAWING

FIG. 2A and FIG. 2B are schematic elevational views of one embodiment of this invention, shown in extended and retracted positions, respectively.

FIGS. 3A and 3B are schematic elevational views of a second embodiment of this invention, shown in extended and retracted positions, respectively.

FIG. 5 is a schematic diagram for explaining imaging and control aspects of this invention.

Figure 1:
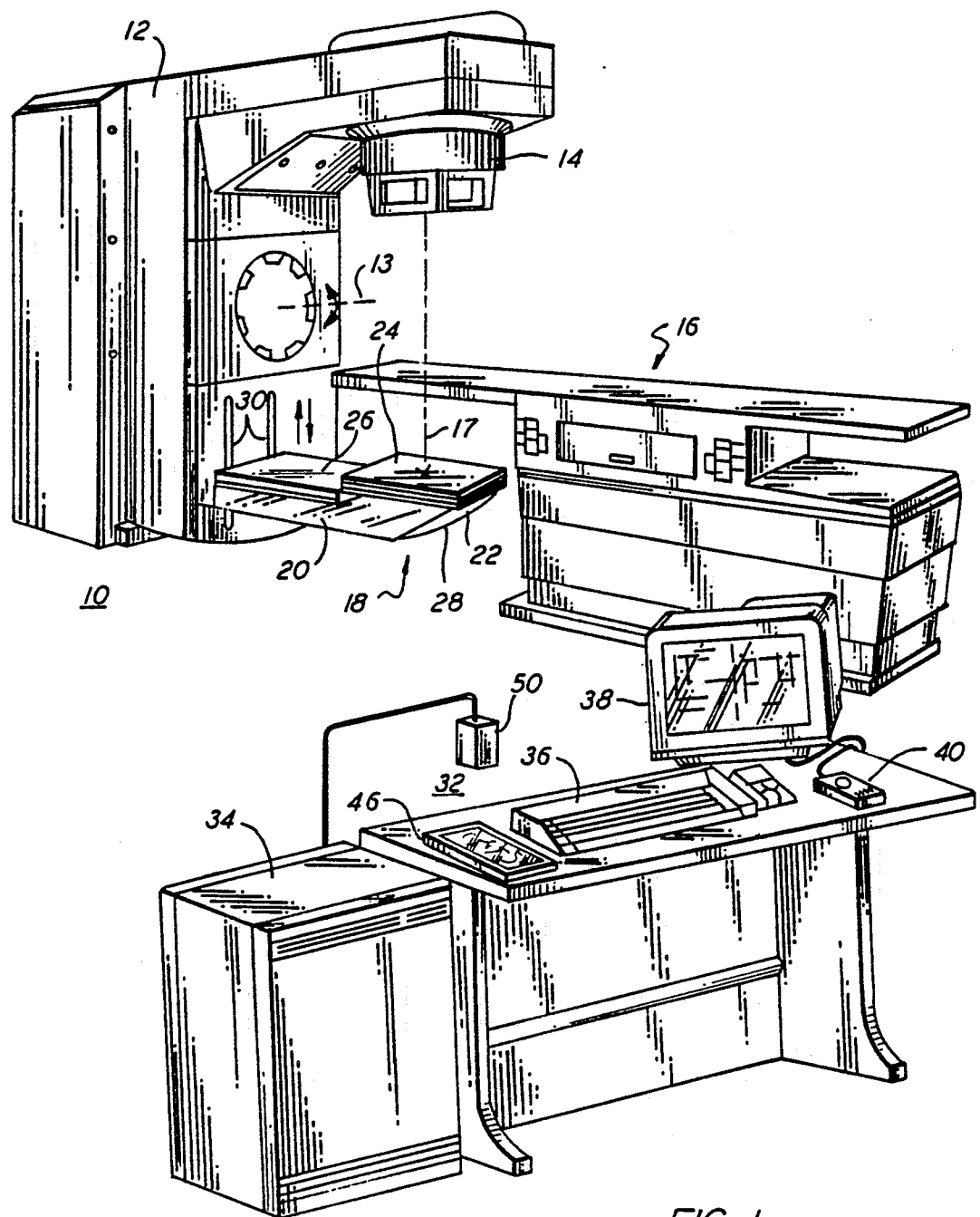
FIG. 1 is a general perspective view of showing a radiation treatment machine on which there is installed an imaging apparatus according to an embodiment of this invention, and also showing a remote console.

DETAILED DESCRIPTION OF THE PREFERRED EMBODIMENTS:

With reference to the Drawing, and initially to FIG. 1, a radiology treatment or therapy machine 10 is shown to have a gantry 12 which rotates about a isocentric axis 13. An x-ray treatment head 14, which can have an energy of 6 MeV to 25 MeV, is mounted on the gantry 12 and positioned to emit an x-ray beam radially across the axis 13. A treatment table 16 is provided to place the patient in proper position for administration of an x-ray dose. The treatment head 14 emits its beam with the beam axis 17 passing through the patient on the table 16.

A therapy image detector assembly 18 is mounted on the gantry 12 diametrically opposite the head 14. In this detector assembly, an elongated light-tight box 20 projects axially from the gantry 12 so that a distal end 22 thereof is positioned under the table 16. A fluoroscopic plate 24 is centered on the beam axis 17 facing the head 14. Protective shielding 26 is situated on an upper wall of the box 20 to protect a video camera within the box (and which is not shown in this view) from stray x-ray radiation.

A mirror 28, which is situated at a 45 degree angle with respect to the plate 24, reflects the fluoroscopic image generated by the plate 24 towards the proximal or camera end of the light box 20.

In this embodiment, there are tracks or rails 30 on the gantry 12 to permit radial, i.e., up-and-down movement of the therapy imager 18, so that once the patient is positioned on the table, the fluoroscopic plate 28 can be placed as close as possible to the patient.

A remote console 32 is associated with this equipment, and is favorably placed in an adjacent room outside the treatment room. The console has an associated image computer processor 34 which contains digital processing as well as sufficient memory storage capacity for a number of digitized fluoroscopic images. Also shown on a console are a keyboard 36 and a video display monitor 38. Here, the image on the screen of the monitor 38 is provided from the camera within the elongated box 20. The screen can also display a simulator image, either side-by-side with or superimposed onto the radiation therapy image. A simulator imager control 40, shown on top of the console 32, will be discussed later.

Construction of a collapsible or telescoping therapy imager arrangement according to one embodiment of this invention is shown in FIGS. 2A and 2B. Here, a light box 120 has a distal end section 122, an intermediate section, 123, and a proximal end 124, where each of the sections is slidable on the next. The proximal end section 124 can be either rigidly mounted onto the gantry 12, or mounted on the rails 30. A television camera 125, which is equipped with a zoom lens or a fixed high sensitivity lens, is fixedly disposed within the proximal end section 124. A fixed, front-silvered high reflectance mirror 127 is situated beneath the fluoroscopic plate 24 and reflects the image produced by the plate back by the camera 125. The zoom-lens-equipped camera 125 permits selection of imaging field of view, depending on the treated area of the patient. A small field of view, i.e., higher magnification, is required for the head or neck, a larger field of view, i.e., a lower magnification, is required for the thorax, and a medium or intermediate magnification is required for the pelvis.

This embodiment extends to a horizontal length of about 150 cm to 160 cm or five feet, four inches as shown in FIG. 2, and collapses to a length of about 75 cm or thirty inches, as shown in FIG. 2B.

Another embodiment of this invention is shown in FIGS. 3A and 3B in which similar parts are identified with the same reference numbers, but primed. In this embodiment, the light box 120' has a distal end section 122' an intermediate section 123' and a proximal end section 124' in which is located the camera 125'. However, unlike the previous embodiment, there is a hinged mirror section 127' which swings up to permit the unit to collapse to a total length of about twenty-four inches as shown in FIG. 3B. The hinged mirror section 127' swings down when the light box 120' is fully extended, as shown in FIG. 3A.

Figure 4:
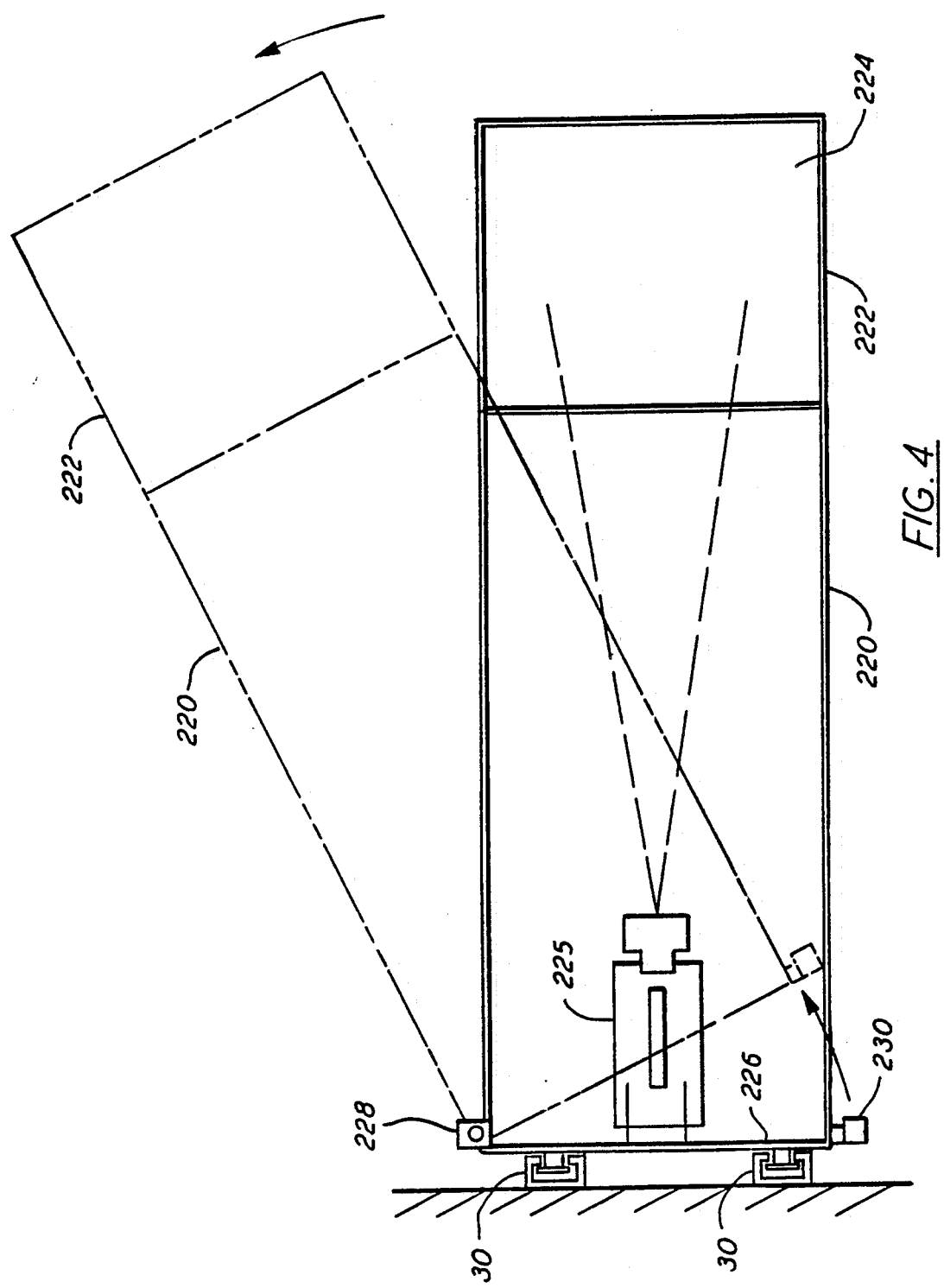
FIG. 4 shows a schematic plan of a third embodiment of this invention in solid lines to show its extended or in use position and in chain lines to show displacement towards its retracted position.

A further embodiment of this invention is shown in FIG. 4, and this embodiment is of generally the same construction as in the previous embodiments, but retracts by swinging to one side, rather than by collapsing. In this embodiment, a light box 220 has a distal end 222 on which a fluoroscopic plate 224 is situated. A camera 225 is affixed onto a proximal end plate 226 that is slidable mounted on the tracks 30. A hinge 228 that has a vertical pivot axis is swingably mounts to one side wall of the box 220 onto the end plate 226. A latch 230 releasably holds the opposite sidewall of the box 220 to the end plate 226. For operational use, the light box 220 is held in the extended position shown in solid lines. The latch 230 releases to permit the box 222 swing to one side. The chain lines indicate the position of the box 220 partially swung away. The interconnection of the radiation therapy imager 18 assembly with the equipment that is located at the console 32 is shown in FIG. 5.

Another embodiment of their invention for the purpose of comparing th esimualator planning imager with the actual treatment images. The zoom-lens-equipped camera 25 is coupled by suitable communications cables to a processor 42 which converts the video images into digital form and stores them in a memory device 44, e.g. a magnetic disk. The simulator image controller 40 is also connected by suitable cabling to the processor, which then controls the translational and angular positioning of x-y translatable and rotatable light table 46. A simulator radiograph 48, i.e. x-ray film, is placed on the light table 46 and its image is picked up by a video camera 50, which is zoomlens equipped. The camera 50 is also coupled by suitable cabling back to the processor 42. In this arrangement, fluoroscopic images picked up by the camera 25 are digitized and stored in the memory device 44. A series of images can be stored here for each patient, and these can each be digitally processed for image enhancement according to any of several known techniques. The simulator image of the radiograph 48 as picked up by the camera 50 is also brought to the processor 42, where the image is digitized and stored, and can be processed as required. The simulator image is then either superimposed on or presented side by side with the treatment image from the camera 25, both images being presented on the display monitor 38. The controller 40 has a track ball to control X and Y translation, thereby controlling the relative position of the radiograph 48 and camera 50. A scale switch SCL controls the zoom feature of the camera 50 to make the image larger or smaller. A focus switch FCS is employed for focusing the camera 50 and a rotation switch RTN is actuated to effect clockwise or counterclockwise rotation of the simulator radiograph 48 relative to the camera 50. By using these control, the radiograph film image can thus be aligned with the therapy image for superimposed comparison. The radiation therapy imaging arrangement as described hereinabove provides immediate high-quality digital imaging for set-up and treatment and provides as well as the advantages of on-on visual verification of patient positioning, on-line visual verification of field alignment and shaping, viewing of live patient images during treatment, and the monitoring of the patient for safety purposes. The stored sequences of images provide feedback for revisions of treatment planning and quality assurance, and also provide a patient image file which is easily stored and retrieved i.e., for patient history purposes.

The acquired image from the radiation therapy imager is of exceptionally high quality and resolution. The fluorescent plate generates an image of about 40 cm by 40 cm, and the video camera 25 has a resolution of 1000 lines, and a signal-to-noise ratio of 63 dB. The detection resolution is at least 1.6 lp/mm with a contrast detectability of 0.5%. In one practical embodiment, the image storage capacity includes 33 MB of solid state RAM, and an on-line hard disk with a capacity of 140 MB. This can be increased to 1200 MB. For large patient files, an optional 60 MB digital streaming tape archive or an optional 1.2 GB optical disk archive can be employed. Preferably the console 32 also includes a film hard copy capability for producing a hard-copy images from the stored images.

While this invention has been described in detail with reference to certain preferred embodiments, it should be understood that the invention is not limited to those precise embodiments. Rather, many modifications and variations would present themselves to those of skill in the art without departing from the scope and spirit of this invention, as defined in the appended claims.

What is claimed is:

1. Radiation therapy imaging apparatus for providing images of a patient being treated on a radiation therapy apparatus for verification and monitoring of patient positioning and verification of alignment and shaping of the radiation field of the radiation therapy apparatus, wherein said radiation therapy apparatus includes a high-energy treatment head for applying a radiation dose to a patient positioned on a treatment table, and a gantry rotatable about an isocentric axis and carrying said treatment head for permitting said radiation dose to be applied to the patient from any of a range of angles about said isocentric axis; the radiation therapy imaging apparatus including a radiation therapy image detector which comprises a video camera mounted on said gantry diametrically opposite said treat head, an elongated light-excluding enclosure enveloping said camera to exclude ambient light from said camera, a fluoroscopic plate positioned on a distal end of said enclosure remote from said camera and aligned with said head to produce a fluoroscopic image in response to radiation applied from said head through said patient, mirror means in said enclosure and oriented for reflecting said image to said camera to permit monitoring on a viewing screen of the positioning of the radiation field in respect to the patient, and means for retracting at least the distal end of said enclosure from a position in which the fluoroscopic plate is disposed opposite the treatment head without disturbing the position of the camera on said gantry, so that said enclosure can be collapsed and kept from projecting under said treatment table when the patient is being positioned on the treatment table.

2. Radiation therapy image detector apparatus according to claim 1, further comprising rail means mounted on said gantry and oriented in a direction generally radially towards and away from said isocentric axis, and means mounting said camera and enclosure and slidably fitting said rail means to permit movement of the camera and enclosure radially with respect to said isocentric axis and towards and away from said treatment head so that said fluoroscopic plate can be positioned as near as possible to the patient on the table.

3. Radiation therapy image detector apparatus according to claim 1, wherein said enclosure is a telescoping arrangement of sections slidably disposed over one another, such that said enclosure can be expanded to maximum length for use and collapsed to minimum length to retract the distal end.

4. Radiation therapy image detector apparatus according to claim 3, wherein said mirror means includes a mirror that is hinged to swing to an operating angle when said enclosure is extended, and to swing out of the way of the telescoping sections on which the distal end of the enclosure is carried when said box is collapsed.

5. Radiation therapy image detector apparatus according to claim 1, wherein said means for retracting includes pivot means mounted on said gantry, and wherein at least the distal end of said enclosure is swingably mounted on said pivot means to permit the distal end of said enclosure to swing to one side.

6. Radiation therapy image detector apparatus according to claim 5, wherein said pivot means swingably mounts one side wall of said enclosure.

7. Radiation therapy image detector apparatus according to claim 6, wherein said retracting means further includes a latch situated on an opposite side wall of said enclosure for releasably holding the enclosure in position with the fluoroscopic plate aligned with the treatment head.

8. Radiation therapy imaging apparatus according to claim 1, further comprising a remote console having a video display device to display said fluoroscopic image as picked up by the video camera, and means to input a simulator image of said patient and to display said simulator image and said fluoroscopic image in a side-by side or superimposed comparison.

9. Radiation therapy image detector apparatus according to claim 8, wherein said remote console includes means for storing a plurality of said fluoroscopic images in digital form.

* * * * *